United States Patent [19]

Smeets et al.

[11] Patent Number: 5,610,040
[45] Date of Patent: Mar. 11, 1997

[54] ENZYMATIC SYNTHESIS OF CERAMIDES AND HYBRID CERAMIDES

[75] Inventors: Jan W. H. Smeets, Vlaardingen; Robertus M. De Pater, Delft; Johannes W. J. Lambers, Pijnacker, all of Netherlands

[73] Assignee: Gist-brocades, n.v., Netherlands

[21] Appl. No.: 367,300

[22] PCT Filed: May 6, 1994

[86] PCT No.: PCT/EP94/01495

§ 371 Date: May 17, 1995

§ 102(e) Date: May 17, 1995

[87] PCT Pub. No.: WO94/26919

PCT Pub. Date: Nov. 24, 1994

[30] Foreign Application Priority Data

May 6, 1993 [EP] European Pat. Off. .............. 93201299

[51] Int. Cl.$^6$ ................................. C12P 13/02; C12N 9/20
[52] U.S. Cl. ......................... 435/129; 435/85; 435/101; 435/128; 435/134; 424/61; 424/70.1; 424/401; 514/844; 514/847; 536/18.6; 536/55.3
[58] Field of Search ........................... 435/128, 129, 435/85, 134, 101; 424/70.1, 61, 401; 514/844, 847; 536/18.6, 55.3

[56] References Cited

U.S. PATENT DOCUMENTS

| | | | |
|---|---|---|---|
| 5,047,337 | 9/1991 | Li et al. | 435/101 |
| 5,270,054 | 12/1993 | Bertolini | 424/401 |
| 5,368,857 | 11/1994 | Corcoran | 424/401 |
| 5,476,671 | 12/1995 | Cho et al. | 424/70.1 |

FOREIGN PATENT DOCUMENTS

| | | | |
|---|---|---|---|
| 0298796A1 | 1/1989 | European Pat. Off. | C12P 13/02 |
| 0420722A3 | 4/1991 | European Pat. Off. | C07C 271/16 |
| 0500437A1 | 8/1992 | European Pat. Off. | C07C 233/20 |

OTHER PUBLICATIONS

Bistline, R. G., Jr. et al., "Lipase Catalyzed Formation of Fatty Amides," *JAOCS* (1991) 68(2):95–98.

Chinsky, N. et al., "Chemoselective Enzymatic Monoacylation of Bifunctional Compounds," *J. Am. Chem. Soc.* (1989) 111:386–388.

Djeghaba, Z. et al., "Enzymes in Organic Synthesis VII: Enzymatic Acylation of Amines," *Tetrahedron Letters* (1991) 32(6):761–762.

Gabin, VIC, "De Nouveaux Outils en Chimie Fine," *Biofutur* (1991) 40–46.

Gotor, V. et al., "Enantioselective Acylation of Amino Alcohols by Porcine Pancreatic Lipase," *J. Chem. Soc., Chem. Commun.* (1988) 957–958.

Hannun, Y. A. and Bell, R. M., "Functions of Sphingolipids and Sphingolipid Breakdown Products in Cellular Regulation," *Science* (1989) 243:500–507.

Imokawa, G. et al., "Water–retaining function in the stratum corneum and its recovery properties by synthetic pseudoceramides," *J. Soc. Cosmet. Chem.* (1989) 40:273–285.

Kerscher, M. et al., "Skin ceramides: structure and function," *European Journal of Dermatology* (1991) 1:39–43.

Margolin, A. L. and Klibanov, A. M., "Peptide Synthesis Catalyzed by Lipases in Anhydrous Organic Solvents," *J. Am. Chem. Soc.* (1987) 109:3802–3804.

Montet, D. et al., "Etude de l'acylation des aminopropanols catalysée par les acyltransférases," *Revue Française des Corps Gras* (1989) 2:79–83.

Montet, D. et al., "Synthesis of N Lauryloleylamide by the Mucor miehei Lipase in an Organic Medium," *Fat Sci. Technol.* (1989) 91(1):14–18.

Zaks, A. and Klibanov, A. M., "Enzyme–catalyzed processes in organic solvents," *Proc. Natl. Acad. Sci. USA* (1985) 82:3192–3196.

*Primary Examiner*—Herbert J. Lilling
*Attorney, Agent, or Firm*—Morrison & Foerster LLP

[57] ABSTRACT

The present invention provides an efficient method for the production of ceramides and hybrid ceramides via the selective N-acylation of glycosphingolipids by reacting an organic acid or ester thereof with a lysosphingolipid in the presence of a lipase in an organic medium.

13 Claims, No Drawings

ENZYMATIC SYNTHESIS OF CERAMIDES AND HYBRID CERAMIDES

The present invention concerns the production of ceramides and hybrid ceramides via the use of lipases to perform the selective acylation of the amino group of lysosphingolipids.

BACKGROUND OF THE INVENTION

Ceramides and derivatives thereof, are of great commercial potential in cosmetics and pharmaceuticals such as hair and skin care products (Zysman, A. et al. European Patent Application 420,722).

Ceramides are a class of polar lipids (sphingolipids) endogenous to the epidermis. Ceramides play a major role in the water-retaining properties of the epidermis. It has been found that topical applications of ceramide- and pseudoceramide- containing compositions are effective in restoring the water content of dry skin and may be effective in relieving atopic eczema (Kerscher, M. et al. (1991) Eur. J. Dermatol., 1, 39–43; Imokawa, G. et al. (1989) J. Soc. Cosmet. Chem., 40, 273–285).

Lysosphingolipids are sphingolipid breakdown products which lack the amide-linked fatty acyl group at the 2-position of the sphingoid base (Hannun, Y. A. and Bell, R. M. (1989) Science 243, 500–507).

In current practice, ceramides are primarily obtained via extraction and isolation from animal epidermal tissues, usually from bovine or porcine epidermal tissue. Obviously, this is a rather costly process on an industrial scale. Moreover, it has been found that these materials are potentially unsafe due to the possible presence of bovine spongiform encephelatis (BSE) in bovine tissue.

Various chemical methods have been published describing the synthesis of ceramides. However, these methods often have the disadvantage of lacking the proper stereochemistry of the thus-produced end-products. Since sphingolipids often have multiple chiral centers, it would be advantageous to employ synthesis methods which reliably provide only a desired stereoisomer, in order to obtain a product which more closely resembles the compound as it appears in nature. Moreover, these chemical synthetic methods may also leave amounts of undesired residual chemical reactants in the final products.

The use of enzymes in chemical synthesis to produce amides in organic solvent has been described (Zaks, A. and Klibanov, A. M. (1985) Proc. Natl. Acad. Sci. U.S.A., 82, 3192–3196). The enzymes most employed for this purpose are lipases (triacylglyceride ester hydrolases; EC 3.1.1.3) and esterases.

Margolin, A. L. and Klibanov, A. M. ((1987) J. Am. Chem. Soc., 109, 3802–3804) studied lipase-catalyzed peptide synthesis in anhydrous organic solvents. Porcine pancreatic lipases (PPL) and mold lipases were found to catalyze the synthesis of peptide bonds in toluene and tetrahydrofuran (THF). Despite the author's assertion that mold lipases have an efficiency comparable to that of PPL in peptide synthesis, we have found that mold lipases were unsuccessful in catalyzing the amidation of lysosphingolipids (a class of amino alcohols) in the synthesis of ceramides.

Bistline, R. G. et al ((1991) JAOCS, 68, 95–98) studied the lipase catalyzed formation of fatty amides. It was found that the three lipase preparations studied showed different degrees of activity and selectivity where hexane was used as the organic solvent. It was also acknowledged that the use of other solvents may produce different results.

Djeghaba, Z. et al ((1991) Tetrahedron Lett., 32, 761–762) reported that, in the enzymatic acylation of amides in ethyl butyrate, a Candida lipase SP 382 was more efficient than lipases from *Candida rugosa*, porcine pancreatic lipase, Pseudomonas lipase and horse-liver acetonic powder. This further demonstrates the enzyme- and solvent- dependent factors which affect lipase-catalyzed amidation reactions.

The use of lipases on reactants having multiple functional groups such as amino alcohols have also been reported. The product formation was found to depend largely on the type of lipase used and the solvent in which the reaction was performed. The results found in these articles clearly demonstrate the unpredictability of the use of various enzymes and solvent systems in the attempt to produce desired acylation products.

Montet, D. et al ((1989) Revue Francaise des Corps Gras, 36, 79–83) studied the acylation of aminopropanols using *Mucor miehei* lipase in organic solvent. The selectivity of the acylation (N- or O- acylation) was found to be influenced by the type of solvent used in the reaction medium. This particular lipase, however, failed to produce a positive result when employed in amidation reactions of lysosphingolipids in the synthesis of ceramides.

Graille, J. et al (European Patent Application 298,796) disclose the synthesis of the fatty acid amide by enzymatic catalysis. The specification teaches that lipases, acylases, peptidases, proteinases and amidases all may be used in the disclosed method. Only *Mucor miehei* lipase was actually exemplified. We have found that this lipases is ineffective in the amidation of lysosphingolipids.

Montet, D. et al ((1989) Fat Sci. Technol., 91, 14–18) have also published another study of the effect of water activity on the synthesis of N-lauryloleylamide using *Mucor miehei* lipase in various solvents. As mentioned above, this lipase failed to produce a positive result when used for the synthesis of ceramides.

Gotor, V. et al (1988) J. Chem. Soc., Chem. Commun., 957–958) described the enantioselective acylation of amino alcohols by porcine pancreatic lipase in organic solvents. Ethyl acetate was found to provide enantioselective results. However, other solvents such as chloroform, benzene and THF did not give satisfactory results.

Chinsky, N. et al ((1989) J. Am. Chem. Soc., 111, 386–388) described the chemoselective enzymatic monoacylation of bi-functional compounds. Surprisingly, O-acylation products predominated when certain amino alcohols were acylated via the use of porcine pancreatic and Pseudomonas lipases in tert-amyl alcohol.

Gagin, V. I. C. ((1991) Biofutur, 40–46) disclosed the successful acylation of amino sugars using *Mucor miehei* lipase in tert-amyl alcohol. These conditions were found to be unsuitable for the amidation of lysosphingolipids.

The foregoing descriptions of the publications forming the state of the art at the present time show the unpredictable nature of the synthesis of amides using various enzymes and solvent systems.

Until now, a reliable method of producing ceramides using enzymatic activity has not been described.

SUMMARY OF THE INVENTION

The present invention provides an efficient process for the production of N-acylated sphingolipids, especially ceramides and hybrid ceramides, via the selective lipase-catalyzed acylation of the free amino group of lysosphingolipids.

According to the present invention, ceramides and hybrid ceramides are produced by reacting an organic acid, or an ester thereof, with a lysosphingolipid in the presence of a bacterial or mammalian lipase and in an organic medium.

The process according to the present invention reliably provides the desired ceramide or hybrid ceramide having the proper stereochemistry, and furthermore, provides the desired end-product without the unwanted co-extraction of bovine spongiform encephalitis or undesirable residual chemicals.

DETAILED DESCRIPTION OF THE INVENTION

According to the present invention, a method for the production of ceramides and hybrid ceramides is provided wherein a lysosphingolipid is amidated with an organic acid or ester thereof via the action of a bacterial or mammalian lipase. The reaction is carried out in an organic medium.

According to the present invention, ceramides are intended to comprise the naturally-occurring sphingolipids normally found in mammalian skin (Kerscher et al., supra).

Hybrid ceramides are ceramide-like sphingolipid compounds, wherein the N-acyl group is other than those found in naturally-occurring ceramides. Such hybrid ceramides may be designed on the basis of an improved ability to be formulated in cosmetic or pharmaceutical preparations for use in skin or hair treatment, and/or an improved ability to be absorbed into the skin or hair of a mammal being treated with a formulation containing these compounds.

Lysosphingolipids are defined in the context of the present invention to comprise a parental sphingolipid which lacks the amide-linked acyl group at the 2-position. All lysosphingolipids contain a charged amine at position 2 and a hydrophobic hydrocarbon tail (see Hannun and Bell, supra, p. 502).

Preferred lysosphingolipids according to the present invention are sphingosine, dihydrosphingosine and phytosphingosine. All are commercially available.

Salts of lysosphingolipids, such as the commercially available HCl and sulphate salts may also be used. However, the salt group should be removed prior to using the free lysosphingolipid. Such removal may be carried out by conventional means such as a pre-treatment with a base such as NaOH.

Organic acids (or esters thereof) to be used in the amidation reaction of the present invention are those of the formula:

R—COOH wherein

R is a straight chain or branched alkyl group having up to 55 carbon atoms, preferably 6 to 50 carbon atoms, and more preferably 14 to 48 carbon atoms, the alkyl chain may optionally be interrupted by an oxygen atom or by an internal ester group; may optionally contain one or more double bonds; and may optionally be substituted with one or more protected hydroxyl moieties.

Protecting groups for the optional hydroxyl moiety are well known in the art and may be selected from appropriate groups as disclosed in Greene, T. (1981) *Protective Groups in Organic Synthesis* (John Wiley & Sons; New York). In preferred embodiments, hydroxyl groups are protected as acetyl esters or methoxy methyl ethers.

Esters of the organic acids to be used in the process according to the present invention are short chain or branched hydrocarbon esters, preferably those of one to five carbon atoms.

Surprisingly, it has been found that a number of lipases described in the literature as being capable of successfully catalyzing the amidation of amines, even certain amino alcohols, were found to be ineffective in the process of the present invention. Yeast and fungal lipases such as those obtainable from *Mucor miehei*, *Humicola lanuginosa* and *Rhizopus arrhizus* were unsuccessful when tested under the reaction conditions of the present invention.

Lipases which were found to be efficacious in the reaction conditions of the present invention are obtainable from bacterial and mammalian species. Preferred bacterial lipases for use in the present invention are obtainable from *Pseudomonas sp.*, especially those obtainable from *Pseudomonas alcaligenes* and *Pseudomonas gladioli*. A preferred mammalian lipase is porcine pancreatic lipase.

The lipase may optionally be immobilized on a solid support such as are well known in the art.

The dosage of lipase added to the reaction is between about 500 to about 2,500 lipase activity units (MLU) per milligram lysosphingolipid and preferably about 1,000 to about 2,000 MLU per mg lysosphingolipid.

Lipase activity units (MLU) may be determined on the basis of the hydrolysis of olive oil. The hydrolysis is measured at 30° C. in a pH-stat containing 3.3% olive oil in a 0.4 mM Tris buffer (pH 9) containing gum arabic (8 g/l), desoxycholate (5 g/l) and sodium chloride (0.6 g/l). One MLU is defined as the amount of enzyme which is required to release one micromole fatty acid per minute under the reaction conditions of the test.

Apart from the selected lipase, the choice of organic medium has also been found to be critical to the present invention. Cyclohexane, which has been disclosed in the literature for use in enzyme-catalyzed amidation reactions, was found to be unsuitable for use in the present invention.

As organic medium, the organic solvents toluene, tert-butyl methyl ether, dimethyl formamide and chloroform gave only moderately acceptable results when employed in the process of the present invention. Of these, tert-butyl methyl ether gave the best results.

Remarkably, it has been found that tetrahydrofuran (THF) was by far the best medium for carrying out the process of the present invention. The best results were obtained from THF which had been dried prior to use.

The organic medium should be substantially anhydrous, that is, have as low a water content as possible. The solvent used as the organic medium may be dried prior to use by conventional means such as distillation, molecular sieves (preferably 4 Å), calcium hydride and lithium aluminum hydride. It has also been found that good results may be obtained by including a drying agent (such as molecular sieves) in the organic reaction medium during the process of the present invention to ensure that the reaction medium remains as anhydrous as possible.

According to the present invention, the organic acid is normally present in slight excess amounts in relation to the lysosphingolipid starting material. Preferably, the molar ratio of the organic acid to the lysosphingolipid is about 1:1 to about 2:1 and more preferably about 1.1:1 to 1.2:1.

The reaction is optimally carried out at a temperature from room temperature (about 20° C.) to about 70° C. and preferably in the range of about 25° to about 65° C. (reflux of THF) and most preferably at about 35° C. to about 65° C. (reflux of THF).

The reaction may be monitored for completion by means such as thin-layer chromatography to determine the presence of lysosphingolipid starting materials. If any of this starting material should remain unreacted, an additional solution of organic acid and lipase, or simply additional lipase, may be prepared separately and added to the reaction solution to drive to reaction to completion and provide optimal yield.

Once the reaction is determined to be complete, as indicated by the exhaustion of the lysosphingolipid starting material, the end-product, normally a solid precipitate, is removed from the reaction solution by conventional means such as filtration. The precipitate may then be rinsed and, if desired, further purified by conventional means known to those skilled in the art such as chromatography and/or recrystalization.

Either prior to the final work-up of the end-product, or subsequent to its purification, deprotection of any protected alcohol groups may be performed according to conventional methods such as those described by Greene et al (supra).

NMR analysis may be used to demonstrate that the correct stereoisomer of the desired ceramide is produced by the process according to the present invention. The "correct stereoisomer" intends that the product obtained by the process of the present invention has the same stereo-chemistry as the sphingoid bases of ceramides found in nature.

Once obtained, the ceramides and hybrid ceramides synthesized according to the present invention may advantageously be used in cosmetic and pharmaceutical preparations for the treatment of the skin or hair. Ceramide-containing preparations are well known in the art.

Alternatively, the ceramides and hybrid ceramides produced according to the present invention may be used as intermediates for further use in other reactions. For example, ceramides produced according to the present invention may subsequently be glycosylated in order to produce sphingomyelins, cerebrosides and gangliosides, among other useful compounds. Furthermore, ceramide 6II, obtainable from the process of the present invention, may be used as a starting material for the synthesis of ceramide 6I according to methods known in the art.

The following examples are provided so as to give those of ordinary skill in the art a complete disclosure and description of how to make and use the invention and are not intended to limit the scope of what the inventors regard as their invention. Efforts have been made to ensure accuracy with respect to numbers used (e.g., amounts, temperature, etc.) but some experimental errors and deviation should be accounted for. Unless indicated otherwise, temperature is in degrees Centigrade and pressure is at or near atmospheric.

EXAMPLE 1

A mixture of 300 mg (0.88 mmol) phytosphingosine, 425 mg (1.4 mmol) methyl stearate, 300 mg *Pseudomonas alcaligenes* lipase M1 (Gist-brocades, Delft, NL) and 600 mg molecular sieves (4 Å; max. 50 micron) in 15 ml THF (pre-dried over calcium hydride) was brought to reflux temperature (65° C.) and stirred for three days.

A white solid product (485 mg —78% conversion) was obtained. Further analysis showed that 71% of this product was N-stearoyl phytosphingosine, 17% was N,O-di-stearoyl phytosphingosine and 6% was stearic acid.

EXAMPLE 2

A mixture of 300 mg (0.88 mmol) phytosphingosine, 310 mg (1.0 mmol) methyl stearate, 300 mg *Pseudomonas alcaligenes* lipase M1 (Gist-brocades, Delft, NL) and 600 mg molecular sieves (4 Å; max. 50 micron) in 7.5 ml THF (pre-dried over calcium hydride) was brought to reflux temperature (65° C.) and stirred. After 48 hours, an additional 300 mg lipase M1 was added and the reaction was allowed to procede for an additional 48 hours.

A white solid product (418 mg —67% conversion) was obtained. Further analysis showed that 83% of this product was the desired N-stearoyl phytosphingosine. No di-acyl product formation was observed.

We claim:

1. A process for production of ceramides and hybrid ceramides, which process comprises the steps of reacting a lysosphingolipid in the presence of a lipase, and in an organic medium, with an acid of the formula RCOOH or with an ester thereof, and recovering said ceramide or said hybrid ceramide;

wherein R is straight-chain or branched-chain alkyl group of 1–55C, optionally interrupted by an oxygen atom or by an internal ester group; optionally containing one or more double bonds; and optionally substituted with one or more protected hydroxyl moieties.

2. The process of claim 1 wherein R contains 6–50C.

3. The process of claim 2 wherein R contains 14–48C.

4. The process of claim 1 wherein the lipase is obtainable from a mammalian species.

5. The process of claim 4 wherein the lipase is porcine pancreatic lipase.

6. The process of claim 1 wherein the lipase is obtainable from a bacterium.

7. The process of claim 6 wherein the bacterium is a Pseudomonas.

8. The process of claim 7 wherein the Pseudomonas is *P. alcaligenes* or *P. gladioli*.

9. The process of claim 1 wherein the organic medium comprises an organic solvent selected from the group consisting of tetrahydrofuran, toluene, tert-butyl methyl ether, dimethyl formamide and chloroform.

10. The process of claim 9 wherein the organic solvent is tetrahydrofuran.

11. The process of claim 9 wherein the organic solvent is anhydrous.

12. The process of claim 1 wherein a drying agent is included in the organic medium.

13. The process of claim 1 wherein the lysosphingolipid is sphingosine, phytosphingosine or dihydrosphingosine.

* * * * *